(12) United States Patent
Zhou et al.

(10) Patent No.: US 12,683,026 B1
(45) Date of Patent: Jul. 14, 2026

(54) METHODS, SYSTEMS, AND COMPUTER PROGRAM PRODUCTS FOR SELECTING CRITERIA SUBSETS FOR PERFORMING A MEDICAL NECESSITY REVIEW WITH AUTOMATIC EVIDENCE HIGHLIGHTING

(71) Applicant: Optum, Inc., Minnetonka, MN (US)

(72) Inventors: Fan Zhou, Redmond, WA (US); Carol Cheng, Seattle, WA (US); Ian Gilbert, Arlington, MA (US); Jaimee Hill, Smithville, MO (US); Feili Yu, Shoreline, WA (US)

(73) Assignee: Optum, Inc., Minnetonka, MN (US)

( * ) Notice: Subject to any disclaimer, the term of this patent is extended or adjusted under 35 U.S.C. 154(b) by 341 days.

(21) Appl. No.: 18/193,085

(22) Filed: Mar. 30, 2023

(51) Int. Cl.
*G16H 50/20* (2018.01)
*G06N 3/045* (2023.01)

(52) U.S. Cl.
CPC ............. *G16H 50/20* (2018.01); *G06N 3/045* (2023.01)

(58) Field of Classification Search
CPC ............................... G16H 50/20; G06N 3/045
USPC .......................................................... 705/2
See application file for complete search history.

(56) References Cited

U.S. PATENT DOCUMENTS

| | | | | |
|---|---|---|---|---|
| 10,580,520 | B2 | 3/2020 | Schulte et al. | |
| 2021/0304857 | A1* | 9/2021 | Johansson | G16H 10/60 |
| 2023/0170092 | A1* | 6/2023 | Moon | G16H 40/20 |
| | | | | 705/2 |
| 2023/0368875 | A1* | 11/2023 | Gold | G16H 15/00 |

OTHER PUBLICATIONS

Lyu, W., Dong, X., Wong, R., Zheng, S., Abell-Hart, K., Wang, F., & Chen, C. (2022). A Multimodal Transformer: Fusing Clinical Notes with Structured EHR Data for Interpretable In-Hospital Mortality Prediction. arXiv preprint arXiv:2208.10240. (Year: 2022).*
Lyu, W., Dong, X., Wong, R., Zheng, S., Abell-Hart, K., Wang, F., & Chen, C. (Apr. 2023). A multimodal transformer: Fusing clinical notes with structured ehr data for interpretable in-hospital mortality prediction. In AMIA Annual Symposium Proceedings (vol. 2022, p. 719). (Year: 2023).*
Agarap, A. F. (2018). Deep learning using rectified linear units (relu). arXiv preprint arXiv:1803.08375. (Year: 2018).*
Lentzen, M., Linden, T., Veeranki, S., Madan, S., Kramer, D., Leodolter, W., & Fröhlich, H. (2022). A transformer-based model trained on large scale claims data for prediction of severe COVID-19 disease progression. IEEE journal of biomedical and health informatics, 27(9), 4548-4558. (Year: 2022).*

* cited by examiner

*Primary Examiner* — Winston R Furtado
(74) *Attorney, Agent, or Firm* — MARSHALL, GERSTEIN & BORUN LLP

(57) ABSTRACT

A method includes receiving input information associated with a health record of a patient, the input information comprising a plurality of input variable tokens; embedding the plurality of input variable tokens to generate a plurality of input variable token vectors, respectively; aggregating the plurality of input variable token vectors to generate a patient health record vector; generating, using an artificial intelligence model, an identification of a criterion used for determining an appropriateness of a care plan for the patient based on the patient health record vector; and generating a ranking of respective ones of the plurality of input variable tokens based on how much each of the plurality of input variable tokens contributed to the identification of the criterion.

20 Claims, 8 Drawing Sheets

METHODS, SYSTEMS, AND COMPUTER PROGRAM PRODUCTS FOR SELECTING CRITERIA SUBSETS FOR PERFORMING A MEDICAL NECESSITY REVIEW WITH AUTOMATIC EVIDENCE HIGHLIGHTING

FIELD

The present inventive concepts relate generally to health care systems and services and, more particularly, medical necessity reviews, which are performed for determining the appropriateness of care plans for patients.

BACKGROUND

As part of a workflow for administering care to patients, health care service providers must determine if a treatment plan is clinically justified. InterQual® criteria are often used by providers as a screening tool to determine if the proposed services are clinically indicated and provided in the appropriate level of care. The InterQual criteria, however, are broken down into numerous medical necessity categories with several of the categories including numerous subsets of criteria. Case managers may use a tool to assist them in creating medical necessity reviews for a patient; however, even with the help of the tool, the medical necessity review process can be difficult. For example, in scenarios where an admission diagnosis is not present, a case manager typically is required to create a manual medical review for the admission, which can be time consuming and may be prone to errors. In scenarios where multiple encounter diagnoses are present, the tool may create an automated medical necessity review for each encounter diagnosis, which may overwhelm the case manager as the case manager needs to evaluate multiple potential medical necessity reviews and complete the appropriate one(s). Moreover, it may be difficult for a case manager using the tool to determine which of the many subsets of InterQual criteria to select for performing the medical necessity review.

SUMMARY

According to some embodiments of the inventive concept, a method comprises: receiving input information associated with a health record of a patient, the input information comprising a plurality of input variable tokens; embedding the plurality of input variable tokens to generate a plurality of input variable token vectors, respectively; aggregating the plurality of input variable token vectors to generate a patient health record vector; generating, using an artificial intelligence model, an identification of a criterion used for determining an appropriateness of a care plan for the patient based on the patient health record vector; and generating a ranking of respective ones of the plurality of input variable tokens based on how much each of the plurality of input variable tokens contributed to the identification of the criterion.

In other embodiments, generating the ranking of the respective ones of the plurality of input variable tokens comprises: generating the ranking of the respective ones of the plurality of input variable tokens using an Integrated Gradient (IG) methodology.

In still other embodiments, generating the ranking of the respective ones of the plurality of input variable tokens using the IG methodology comprises: generating a baseline vector; determining a baseline gradient magnitude value of the artificial intelligence model for the baseline vector;

determining a plurality of token gradient magnitude values of the artificial intelligence model for the plurality of input variable token vectors, respectively; determining a plurality of gradient change magnitude values of the artificial intelligence model based on a plurality of differences between the plurality of token gradient magnitude values and the baseline gradient magnitude value, respectively; and generating the ranking of the respective ones of the plurality of input variable tokens based on the plurality of gradient change magnitude values.

In still other embodiments, the baseline vector is not representative of any information that affects generating identification of the criterion using the artificial intelligence model.

In still other embodiments, the method further comprises: generating the plurality of input variable tokens using a bidirectional transformer; wherein embedding the plurality of input variable tokens to generate the plurality of input variable token vectors comprises: embedding the plurality of input variable tokens to generate the plurality of input variable token vectors using the bidirectional transformer.

In still other embodiments, the bidirectional transformer is a Clinical Bidirectional Encoder Representations from Transformers (ClinicalBERT) bidirectional transformer.

In still other embodiments, the method further comprises: generating a mapping between the plurality of input variable tokens and segments of the input information.

In still other embodiments, the method further comprises: generating a ranking of the segments of the input information based on the ranking of the respective ones of the plurality of input variable tokens and the mapping.

In still other embodiments, the segments of the input information comprise sentences, medications, lab tests, and/or procedures.

In some embodiments of the inventive concept, a system comprises: a processor; and a memory coupled to the processor and comprising computer readable program code embodied in the memory that is executable by the processor to perform operations comprising: receiving input information associated with a health record of a patient, the input information comprising a plurality of input variable tokens; embedding the plurality of input variable tokens to generate a plurality of input variable token vectors, respectively; aggregating the plurality of input variable token vectors to generate a patient health record vector; generating, using an artificial intelligence model, an identification of a criterion used for determining an appropriateness of a care plan for the patient based on the patient health record vector; and generating a ranking of respective ones of the plurality of input variable tokens based on how much each of the plurality of input variable tokens contributed to the identification of the criterion.

In further embodiments, generating the ranking of the respective ones of the plurality of input variable tokens comprises: generating the ranking of the respective ones of the plurality of input variable tokens using an Integrated Gradient (IG) methodology.

In still further embodiments, generating the ranking of the respective ones of the plurality of input variable tokens using the IG methodology comprises: generating a baseline vector; determining a baseline gradient magnitude value of the artificial intelligence model for the baseline vector; determining a plurality of token gradient magnitude values of the artificial intelligence model for the plurality of input variable token vectors, respectively; determining a plurality of gradient change magnitude values of the artificial intelligence model based on a plurality of differences between the plurality of token gradient magnitude values and the baseline gradient magnitude value, respectively; and generating the ranking of the respective ones of the plurality of input variable tokens based on the plurality of gradient change magnitude values.

In still further embodiments, the operations further comprise: generating the plurality of input variable tokens using a bidirectional transformer; wherein embedding the plurality of input variable tokens to generate the plurality of input variable token vectors comprises: embedding the plurality of input variable tokens to generate the plurality of input variable token vectors using the bidirectional transformer.

In still further embodiments, the operations further comprise: generating a mapping between the plurality of input variable tokens and segments of the input information.

In still further embodiments, the operations further comprise: generating a ranking of the segments of the input information based on the ranking of the respective ones of the plurality of input variable tokens and the mapping.

In some embodiments of the inventive concept a computer program product comprises a non-transitory computer readable storage medium comprising computer readable program code embodied in the medium that is executable by a processor to perform operations comprising: receiving input information associated with a health record of a patient, the input information comprising a plurality of input variable tokens; embedding the plurality of input variable tokens to generate a plurality of input variable token vectors, respectively; aggregating the plurality of input variable token vectors to generate a patient health record vector; generating, using an artificial intelligence model, an identification of a criterion used for determining an appropriateness of a care plan for the patient based on the patient health record vector; and generating a ranking of respective ones of the plurality of input variable tokens based on how much each of the plurality of input variable tokens contributed to the identification of the criterion.

In other embodiments, generating the ranking of the respective ones of the plurality of input variable tokens comprises: generating a baseline vector; determining a baseline gradient magnitude value of the artificial intelligence model for the baseline vector; determining a plurality of token gradient magnitude values of the artificial intelligence model for the plurality of input variable token vectors, respectively; determining a plurality of gradient change magnitude values of the artificial intelligence model based on a plurality of differences between the plurality of token gradient magnitude values and the baseline gradient magnitude value, respectively; and generating the ranking of the respective ones of the plurality of input variable tokens based on the plurality of gradient change magnitude values.

In still other embodiments, the operations further comprise: generating the plurality of input variable tokens using a bidirectional transformer; wherein embedding the plurality of input variable tokens to generate the plurality of input variable token vectors comprises: embedding the plurality of input variable tokens to generate the plurality of input variable token vectors using the bidirectional transformer.

In still other embodiments, the operations further comprise: generating a mapping between the plurality of input variable tokens and segments of the input information.

In still other embodiments, the operations further comprise: generating a ranking of the segments of the input information based on the ranking of the respective ones of the plurality of input variable tokens and the mapping.

Other methods, systems, articles of manufacture, and/or computer program products according to embodiments of the inventive concept will be or become apparent to one with skill in the art upon review of the following drawings and detailed description. It is intended that all such additional systems, methods, articles of manufacture, and/or computer program products be included within this description, be within the scope of the present inventive subject matter and be protected by the accompanying claims.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
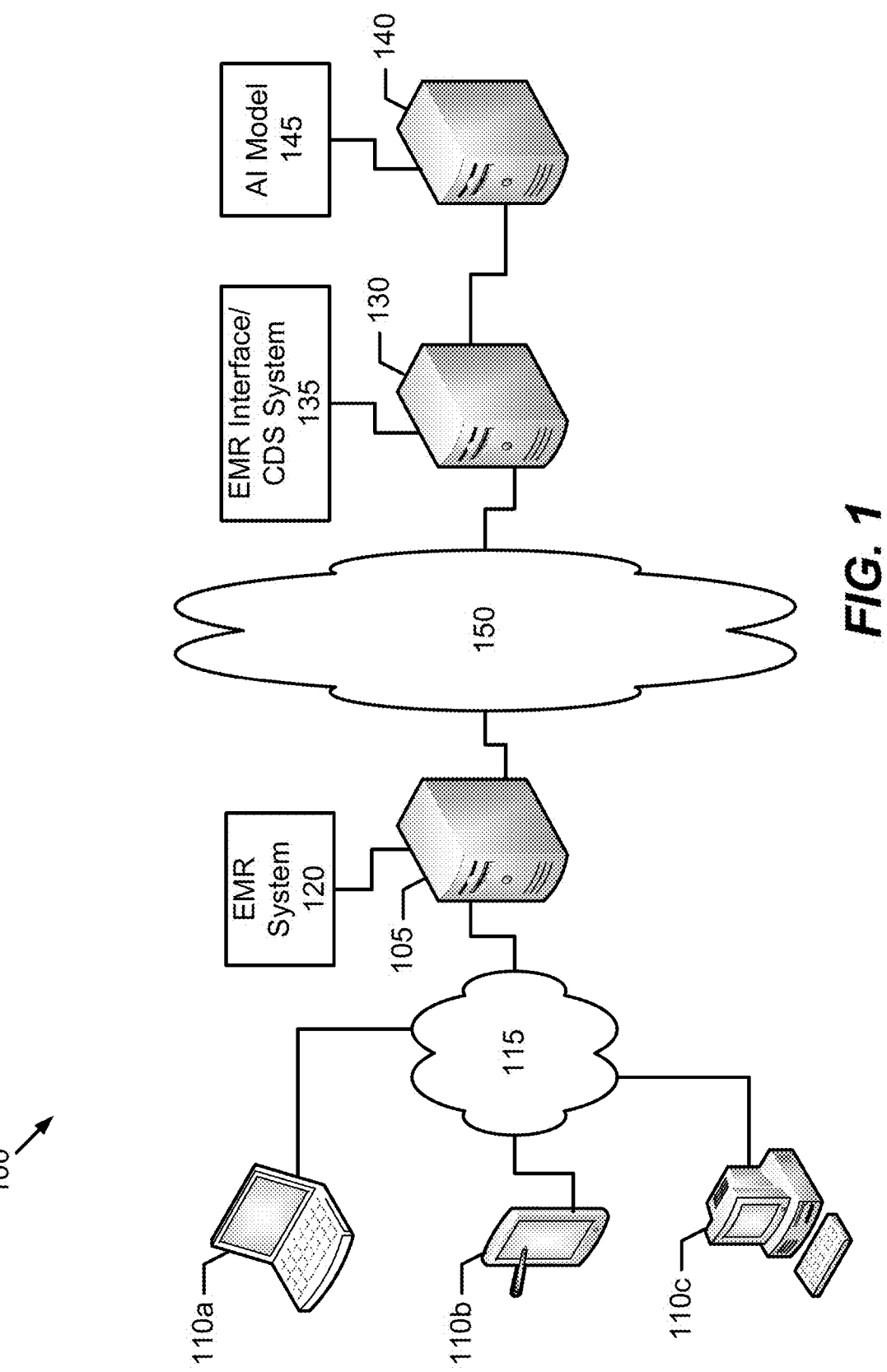
FIG. 1 is a block diagram that illustrates a communication network including an Artificial Intelligence (AI) assisted system with automatic evidence highlighting for selecting criteria subsets for use in a medical necessity review in accordance with some embodiments of the inventive concept.

In the following detailed description, numerous specific details are set forth to provide a thorough understanding of embodiments of the inventive concept. However, it will be understood by those skilled in the art that embodiments of the inventive concept may be practiced without these specific details. In some instances, well-known methods, procedures, components, and circuits have not been described in detail so as not to obscure the inventive concept. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "provider" may mean any person or entity involved in providing health care products and/or services to a patient.

Embodiments of the inventive concept are described herein in the context of an automated system for selecting one or more subsets of criteria used for determining the appropriateness of a care plan for a patient based on the patient's medical record with automatic evidence highlighting indicating what feature(s) in the input dataset had the most impact on the ranking or recommendation. The automated system may include an Artificial Intelligence (AI) model, which uses multi-layer neural network technology. The embodiments of the system for selecting subsets of criteria for a medical necessity review are described with respect to the use of one or more multi-layer neural network systems. It will be understood, however, that embodiments of the inventive concept are not limited to multi-layer neural network implementations of the medical necessity review criteria selection system and that other types of AI systems may be used including, but not limited to, a machine learning system, a deep learning system, a natural language processing system, and/or computer vision system. Moreover, it will be understood that the multi-layer neural network is a multi-layer artificial neural network comprising artificial neurons or nodes and does not include a biological neural network comprising real biological neurons. The AI model described herein may be configured to transform a memory of a computer system to include one or more data structures, such as, but not limited to, arrays, extensible arrays, linked lists, binary trees, balanced trees, heaps, stacks, and/or queues. These data structures can be configured or modified through the AI training process to improve the efficiency of a computer system when the computer system operates in an inference mode to make an inference, prediction, classification, suggestion, or the like with respect to selection of a one or more subsets of criteria used for medical necessity review in response to input information or data provided thereto.

Some embodiments of the inventive concept stem from a realization that it can be difficult for a case manager to select one or more subsets of criteria for use in determining the appropriateness of a care plan for a patient as part of a medical necessity review. For example, the InterQual criteria may have close to one-hundred subsets of criteria spanning multiple medical necessity categories. Selection of the appropriate medical necessity review criteria can be further complicated as a patient may present with no admission diagnosis, which may require more manual intervention in the review for that admission, or the patient may present with multiple encounter diagnoses, which can be overwhelming to the case manager in deciding which diagnoses should be used as a basis for a medical necessity review. AI tools may be used to assist a case manager in selecting criteria subsets for performing a medical necessity review according to some embodiments of the inventive concept. A case manager may, however, still need some indication of what evidence the AI tool relied on in making its recommendations as the recommendations may be difficult to interpret. Some embodiments of the inventive concept may provide an automated medical necessity review criteria selection system that uses an AI model to identify one or more review criterion subsets, such as the InterQual criteria subsets, based on a patient's medical record. When multiple subsets are identified, the subsets may be ranked based on their relevance to determining the appropriateness of the care plan for the patient. The information input to the medical necessity review criteria selection system may include medical record information, such as encounter diagnoses, medications, lab tests, and procedures. This information may be embedded and aggregated to create a patient health care record vector. The AI model may be used to generate an identification of the one or more subsets of criteria used for determining the appropriateness of the care plan for the patient based on the patient health record vector. In addition, one or more of the input variable tokens used by the AI model to generate identification of each of the criterion used for determining the appropriateness of the care plan may be ranked based on how much each of these input variable tokens contributed to the identification of the criterion. In some embodiments, this evidence highlighting may be known as feature attribution and may be based on the use of an Integrated Gradient (IG) methodology. By identifying the particular input variable tokens that were the primary factors in the identification of the one or more criterion by the AI model, a case manager may have more confidence in the criterion identification and any rankings of multiple criteria. Moreover, a case manager need not review the clinical information in the patient's health record to justify the recommendation or ranking by the AI model of the one or more criterion used for determining the appropriateness of the care plan.

Referring to FIG. 1, a communication network 100 including a system for selecting criteria subsets for use in a medical necessity review with automatic evidence highlighting, in accordance with some embodiments of the inventive concept, comprises a health care facility server 105 that is coupled to devices 110a, 110b, and 110c via a network 115. The health care facility may be any type of health care or medical facility, such as a hospital, doctor's office, specialty center (e.g., surgical center, orthopedic center, laboratory center etc.), or the like. The health care facility server 105 may be configured with an Electronic Medical Record (EMR) system module 120 to manage patient files and facilitate the entry of orders for patients via health care service providers ("providers"). Although shown as one combined system in FIG. 1, it will be understood that some health care facilities use separate systems for electronic medical record management and order entry management. The providers may use devices, such as devices 110a, 110b, and 110c to manage patients' electronic records and to issue orders for the patients through the EMR system 120. An order may include, but is not limited to, a treatment, a procedure (e.g., surgical procedure, physical therapy procedure, radiologic/imaging procedure, etc.) a test, a prescription, and the like. The network 115 communicatively couples the devices 110a, 110b, and 110c to the health care facility server 105. The network 115 may comprise one or more local or wireless networks to communicate with the health care facility server 105 when the health care facility server 105 is located in or proximate to the health care facility. When the health care facility server 105 is in a remote location from the health care facility, such as part of a cloud computing system or at a central computing center, then the network 115 may include one or more wide area or global networks, such as the Internet.

According to some embodiments of the inventive concept, providers may access a system for selecting criteria subsets for use in a medical necessity review. The system may be an AI assisted system including an AI model. The AI assisted system may include a health care facility interface server 130, which includes an EMR interface/clinical decision support (CDS) system module 135 to facilitate the transfer of information between the EMR system 120, which the providers use to manage patient records and issue orders, and a criteria subset selection server 140, which includes an AI model module 145. The criteria subset selection server 140 and AI model module 145 may be configured to receive patient information contained in records in the EMR system 120 from the health care facility server 105 and EMR system module 120 by way of the health care facility interface server 130 and EMR interface/CDS system module 135. The EMR interface/CDS system module 135 in conjunction with the AI model module 145 may be further configured to generate identification and/or rankings of criteria subsets for use in a medical necessity review with automatic evidence highlighting in accordance with some embodiments of the inventive concept. It will be understood that the division of functionality described herein between the criteria subset selection server 140/AI model module 145 and the health care facility interface server 130/EMR interface/CDS system module 135 is an example. Various functionality and capabilities can be moved between the criteria subset selection server 140/AI model module 145 and the health care facility interface server 130/EMR interface/CDS system module 135 in accordance with different embodiments of the inventive concept. Moreover, in some embodiments, the criteria subset selection server 140/AI model module 145 and the health care facility interface server 130/EMR interface/CDS system module 135 may be merged as a single logical and/or physical entity.

A network 150 couples the health care facility server 105 to the health care facility interface server 130. The network 150 may be a global network, such as the Internet or other publicly accessible network. Various elements of the network 150 may be interconnected by a wide area network, a local area network, an Intranet, and/or other private network, which may not be accessible by the general public. Thus, the communication network 150 may represent a combination of public and private networks or a virtual private network (VPN). The network 150 may be a wireless network, a wireline network, or may be a combination of both wireless and wireline networks.

The service provided through the health care facility interface server 130, EMR interface/CDS system module 135, criteria subset selection server 140/AI model module 145 to provide medical necessity review criteria selection support may, in some embodiments, be embodied as a cloud service. For example, health care facilities may integrate their EMR systems/order systems with the medical necessity review criteria selection support service and access the service as a Web service. In some embodiments, the medical necessity review criteria selection support service may be implemented as a Representational State Transfer Web Service (RESTful Web service).

Although FIG. 1 illustrates an example communication network including a medical necessity review criteria selection system with automatic evidence highlighting, it will be understood that embodiments of the inventive subject matter are not limited to such configurations, but are intended to encompass any configuration capable of carrying out the operations described herein.

Figure 2:
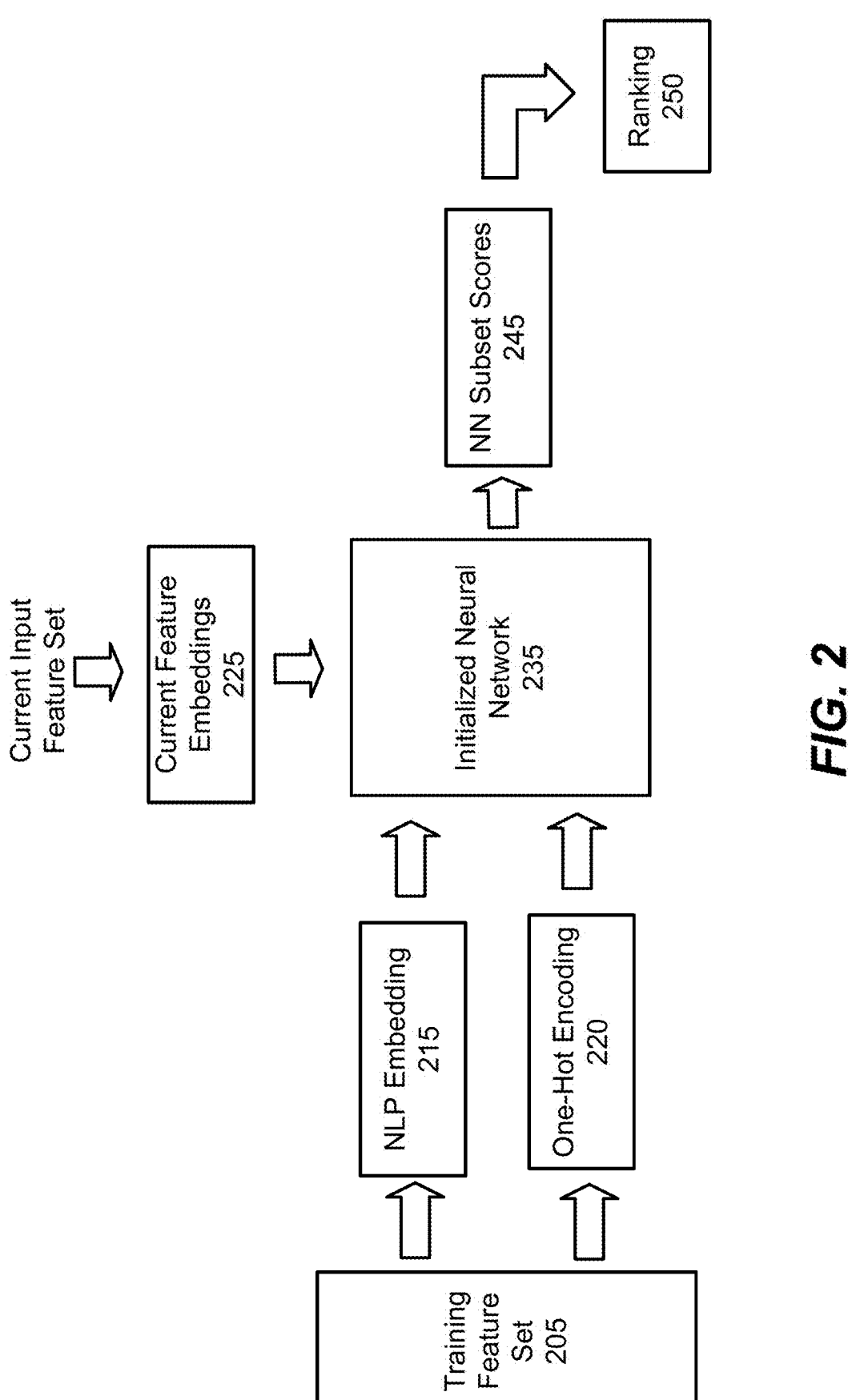
FIG. 2 is a block diagram of the AI system of FIG. 1 in accordance with some embodiments of the inventive concept.

FIG. 2 is a block diagram of an AI model used in the medical necessity review criteria selection system of FIG. 1 in accordance with some embodiments of the inventive concept. As shown in FIG. 2, a training feature set 205 for training and/or initializing the AI model may include information associated with a plurality of input variables, which include, but are not limited to, encounter diagnoses, medications, lab tests, and procedures. A Natural Language Processing (NLP) embedding module 215 may be used to create embeddings for the input variables contained in the input feature set 205 along with the criteria subsets. An embedding is a learned continuous vector representation of a discrete variable. These input variables from the training feature set 205 may be categorical or discrete variables for which a continuous vector is generated. Similarly, the multi-layer neural network 235 is initialized or trained using the embeddings provided by the NLP embedding module 215 and the one-hot encoding module 220, which may be used to create embeddings for lab test information, for example.

In some embodiments, the NLP embedding module 215 may comprise a bidirectional transformer, such as a Clinical Bidirectional Encoder Representations from Transformers (ClinicalBERT) bidirectional transformer. ClinicalBERT is trained on clinical notes/electronic health records and may capture qualitative relationships among clinical concepts in a database of medical terms.

Figure 3:
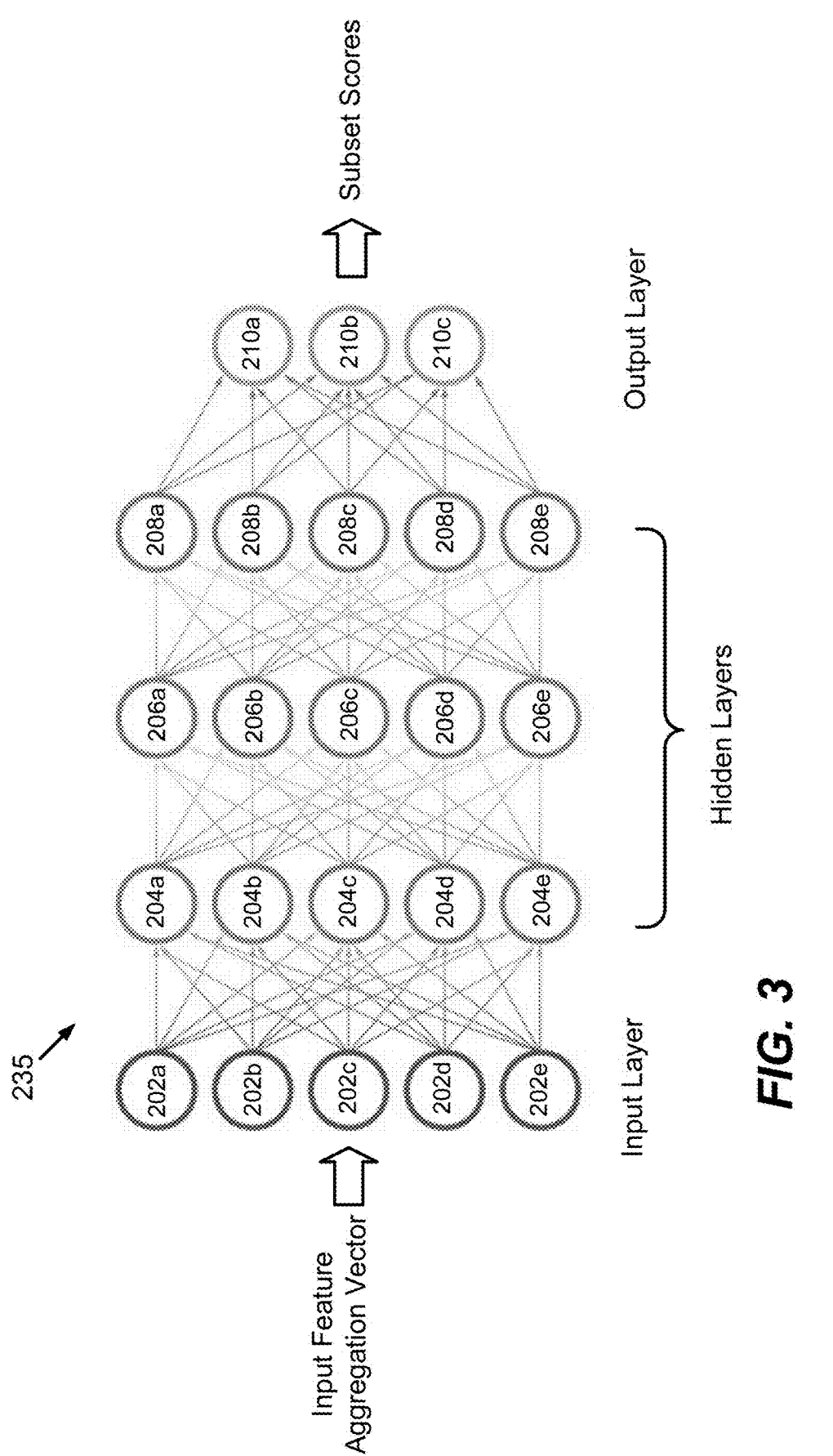
FIG. 3 is a block diagram of a neural network used in the AI model of FIGS. 1 and 2 in accordance with some embodiments of the inventive concept.

FIG. 3 is a diagram of an initialized artificial neural network system 235 according to some embodiments of the inventive concept. As shown in FIG. 3, the artificial neural network 235 includes a plurality of node layers comprising an input layer, one or more hidden layers, and an output layer. In the example shown in FIG. 3, an input layer comprises five nodes or neurons 202*a*, 202*b*, 202*c*, 202*d*, and 202*e* and an output layer comprises three nodes or neurons 210*a*, 210*b*, and 210*c*. In the example shown, three hidden layers connect the input layer to the output layer including a first hidden layer comprising five nodes or neurons 204*a*, 204*b*, 204*c*, 204*d*, and 204*c*, a second hidden layer comprising five nodes or neurons 206*a*, 206*b*, 206*c*, 206*d*, and 206*c*, and a third hidden layer comprising five nodes or neurons 208*a*, 208*b*, 208*c*, 208*d*, and 208*c*. Other embodiments may use more or fewer hidden layers. Each node or neuron connects to another and has an associated weight and threshold. If the output of any individual node or neuron is above the specified threshold value, that node is activated, sending data to the next layer of the network. Otherwise, no data is passed along to the next layer of the network.

The number of nodes in the input layer 202*a*, 202*b*, 202*c*. 202*d*, and 202*e* may correspond to the number of variables in the training feature set 205 during training and the current input feature set during inference mode. In aggregate, the embedded vectors corresponding to the plurality of input variables may be viewed as a patient health record vector. The number of nodes in the output layer 210*a*. 210*b*, and 210*c* may correspond to the number of different criteria subsets for use in a medical necessity review that are identified and/or scored/ranked using the neural network 235. The subsets may be, for example, subsets of the InterQual criteria in some embodiments. While only three nodes 210*a*, 210*b*, and 210*c* are shown in FIG. 3, the number of output layer nodes would typically be much greater due to the large number of criteria subsets that are defined for performing medical necessity reviews. In aggregate, the embedded vectors of the different criteria subsets may be viewed as an aggregated subset vector.

As described above, the multi-layer neural network 235 relies on training data to learn and improve its accuracy over time. The multi-layer neural network 235 may be trained to identify and/or score criteria subsets for use in a medical necessity review based on input information associated with a patient's medical record. Historical patient medical records may be used in the training, knowledge base, and/or vocabulary for the artificial neural network 235, the NLP embedding module 215, and the one-hot encoding module 220. Once the various parameters of the multi-layer neural network 235 are tuned and refined for accuracy, it can be used, among other applications, to generate inferences or scores for criteria subsets for use in a medical necessity review in response to input data associated with a patient, including free-text queries. Such a multi-layer neural network 235 may also be trained to perform other tasks, such as, but not limited to, classify images, recognize and interpret speech, and cluster data, amongst other uses.

Each individual node or neuron may be viewed as implementing a linear regression model, which is composed of input data, weights, a bias (or threshold), and an output. Once an input layer is determined, weights are assigned. These weights help determine the importance of any given variable, with larger ones contributing more significantly to the output compared to other inputs. All inputs are then multiplied by their respective weights and then summed, i.e., a MAC operation. In FIG. 3, node or neuron 206a, for example, receives inputs corresponding to the outputs of nodes or neurons 204a, 204b, 204c. 204d, and 204c. These inputs are multiplied by their corresponding weights and summed at node or neuron 206a. Afterward, the output is passed through an activation function, which determines the output. If that output exceeds a given threshold, it activates the node by passing data to the next layer in the network. This results in the output of one node becoming the input of the next node. This process of passing data from one layer to the next layer is an example of a feedforward artificial neural network. Some embodiments of the inventive concept may provide a rectified linear unit (ReLU) activation function for use at one or more of the multi-layer neural network 235 nodes.

Returning to FIG. 2, once multi-layer neural network 235 is trained, the multi-layer neural network 235 may operate in inference mode based on a current input feature set for a current patient. The current input feature set may include information associated with one or more of the plurality of input variables used in the training feature set 205. The current feature set are embedded into a plurality of input variable vectors using the current feature embeddings module 225, which are then aggregated to provide a patient health record vector. The multi-layer neural network 235 may then process the patient health record vector to generate confidence scores for the different criteria subsets for use in a medical necessity review, which is represented by the neural network subset confidence scores 245. These confidence scores 245 may be termed similarity scores, which may be indicative of a similarity between the patient health record vector, which comprises an aggregation of the input variable vectors, and the aggregated subset vector, which is the aggregation of the vectors associated with the criteria subsets. The individual similarity scores may be based on the similarity between the patient health record vector and the individual medical criteria subset vectors from, for example, the output layer 210a, 210b, 210c of the multi-layer neural network 235. In some embodiments, cosine similarity score(s) may be generated between the patient health record vector and the aggregated subset vector and may be used to rank 250 the various criteria subsets in terms based on their probability of being relevant or applicable to the input information from the patient's medical record, i.e., the information associated with the input variables.

Figure 4:
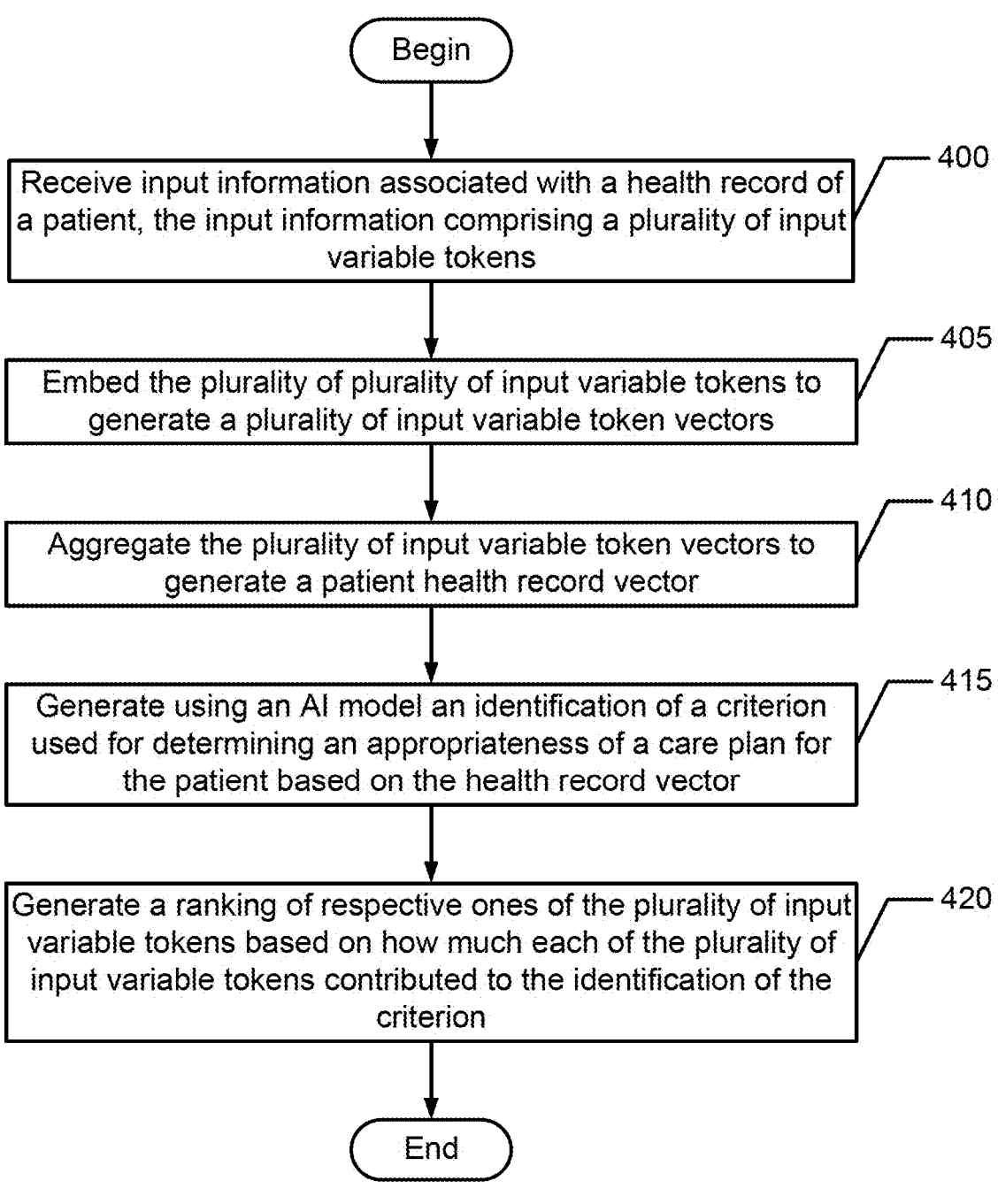
FIGS. 4-7 are flowcharts that illustrate operations for selecting criteria subsets for performing a medical necessity review with automatic evidence highlighting using the AI system of FIGS. 1 and 2 in accordance with some embodiments of the inventive concept.

FIGS. 4-7 are flowcharts that illustrate operations for selecting criteria subsets for performing a medical necessity review with automatic evidence highlighting using the AI system of FIGS. 1 and 2 in accordance with some embodiments of the inventive concept. Referring now to FIG. 4, operations begin at block 400 where input information associated with a health record of a patient is received. This information is associated with a plurality of input variable tokens. The information may be, for example, one or more input variable values for the input variables of the training feature set 205 described above, which may correspond to the current input feature set of FIG. 2. The input information associated with the plurality of input variable tokens may be embedded using the current feature embeddings module 225 to generate a plurality of input variable token vectors, respectively, at block 405. In some embodiments, the current feature embeddings module 225 may comprise a bidirectional transformer, such as a ClinicalBERT bidirectional transformer, as described above with respect to the NLP embedding module 215. The plurality of input variable token vectors may be aggregated to generate a patient health record vector at block 410. At block 415, a ranking of one or more of the plurality of subsets of criteria used for determining the appropriateness of the care plan for the patient may be generated using an AI engine, such as, for example, the multi-layer neural network 235. To assist a case manager, for example, in understanding what features in the current input data set had the greatest effect in identifying criterion subset or criteria subsets for determining the appropriateness of the care plan, a ranking of one or more of the respective ones of the plurality of input variable tokens based on how much each of the plurality of input variable tokens contributed to the identification of each of the one or more criteria may be generated at block 420.

Figures 5, 6:
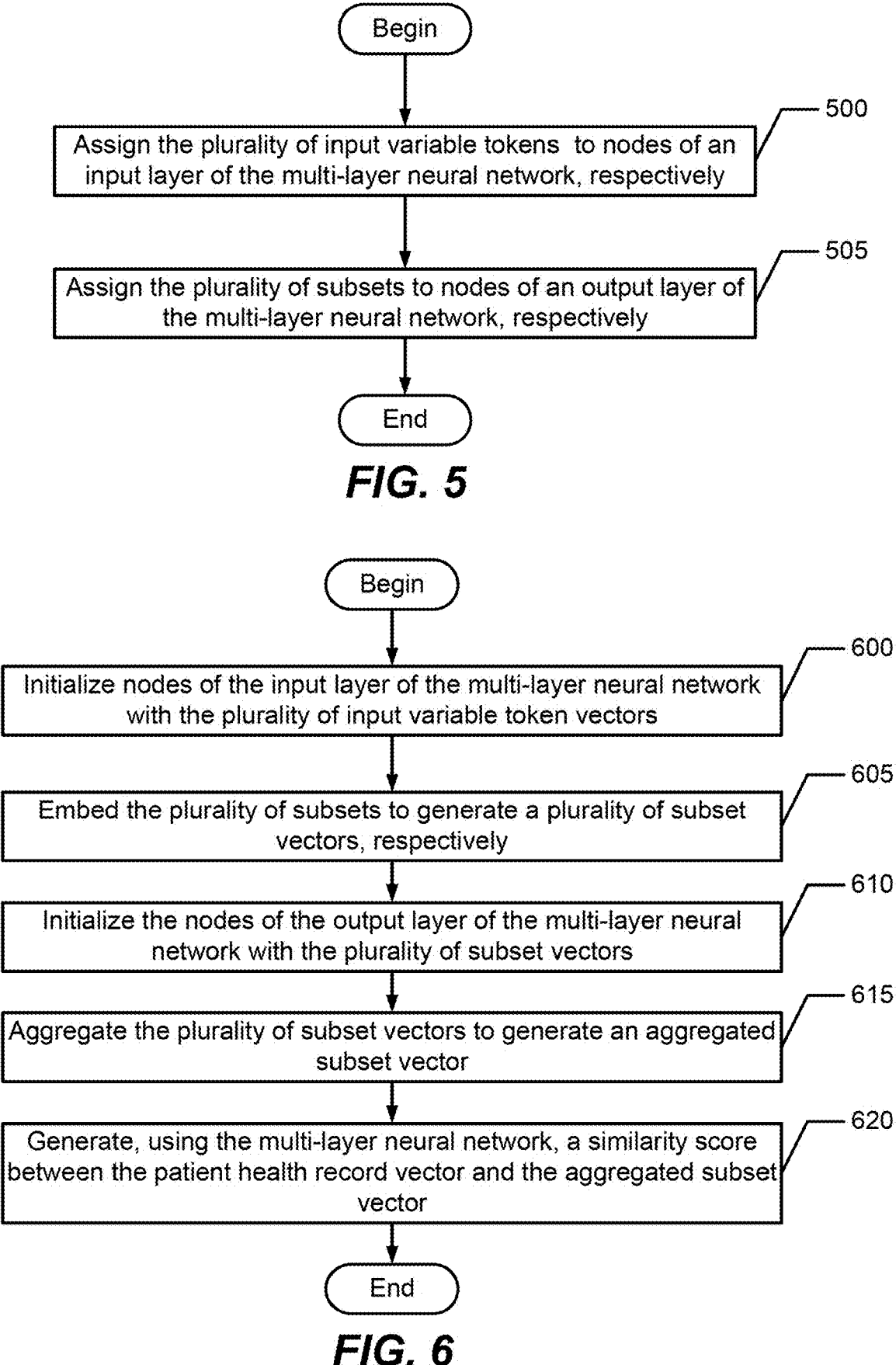

Referring now to FIG. 5, example operations of the multi-layer neural network 235 begin at block 500 where the plurality of input variable token vectors are assigned to the input layer nodes of the neural network 235. The plurality of criteria subsets for use in a medical necessity review is assigned to nodes of the output layer of the multi-layer neural network 235 at block 505. Referring now to FIG. 6, the nodes of the input layer of the multi-layer neural network 235 are initialized with the plurality of input variable token vectors at block 600. The plurality of criteria subsets is embedded using, for example, the NLP embedding module 215, at block 605 to generate a plurality of subset vectors, respectively. The nodes of the output layer of the neural network 235 are initialized with the plurality of subset vectors, respectively, at block 610. The plurality of subset vectors is aggregated to generate an aggregated subset vector at block 615. A similarity score between the patient health record vector and the aggregated subset vector may be generated at block 620 using the multi-layer neural network 235. The similarity score may be, for example, a cosine similarity score in some embodiments of the inventive concept. A plurality of similarity scores may be generated between the patient health record vector and the individual subset vectors, which are indicative of the probability that the subset criteria are relevant or applicable to the patient's health record when performing a medical necessity review as part of forming a care plan for the patient. When multiple criteria subsets are identified and ranked, a case manager may, for example, select one or more of the higher ranked criteria subsets in performing a medical necessity review to determine the appropriateness of the care plan for the patient.

But as described above, a case manager may want to understand what features in the input information had the greatest impact on the multi-layer neural network model's 235 identification and/or ranking of the one or more criteria subsets. This evidence identification may be referred to as feature attribution, which applies generally to any AI model. Specifically, feature attributions indicate how much each feature in the AI model contributed to any prediction, inference, categorization, recommendation, or the like. In some embodiments, the evidence highlighting through feature attribution may be provided using an IG methodology.

IG can be used to assign an attribution value to each input feature, which is indicative of how much the input contributed to the final prediction, inference, categorization, recommendation, or the like. When the input feature tokens are based on text identified through NLP, the goal may be to identify which segments of the text, e.g., sentences, have the most impact on the output of the AI model. The IG methodology begins with a baseline vector, which is not representative of any information that affects the output of the AI model. When the input is text, the baseline vector may correspond to the sentence start and sentence end tokens. A number of steps are defined for getting from the baseline token vector to the AI model output. In some embodiments, each step may correspond to an input variable token. For each step or input variable token, the model may output its prediction, inference, categorization, recommendation, or the like. This may provide an attribution value for each input feature, which is indicative for how much the feature influenced the overall result of the AI model.

The size of the steps referred to above in the IG methodology may be indicative of the magnitude of the change in gradient based on the difference between an input feature token vector and the baseline vector. The IG methodology, therefore, is applicable to AI models, such as multilayer neural networks that use an activation function that is differentiable.

Figure 7:
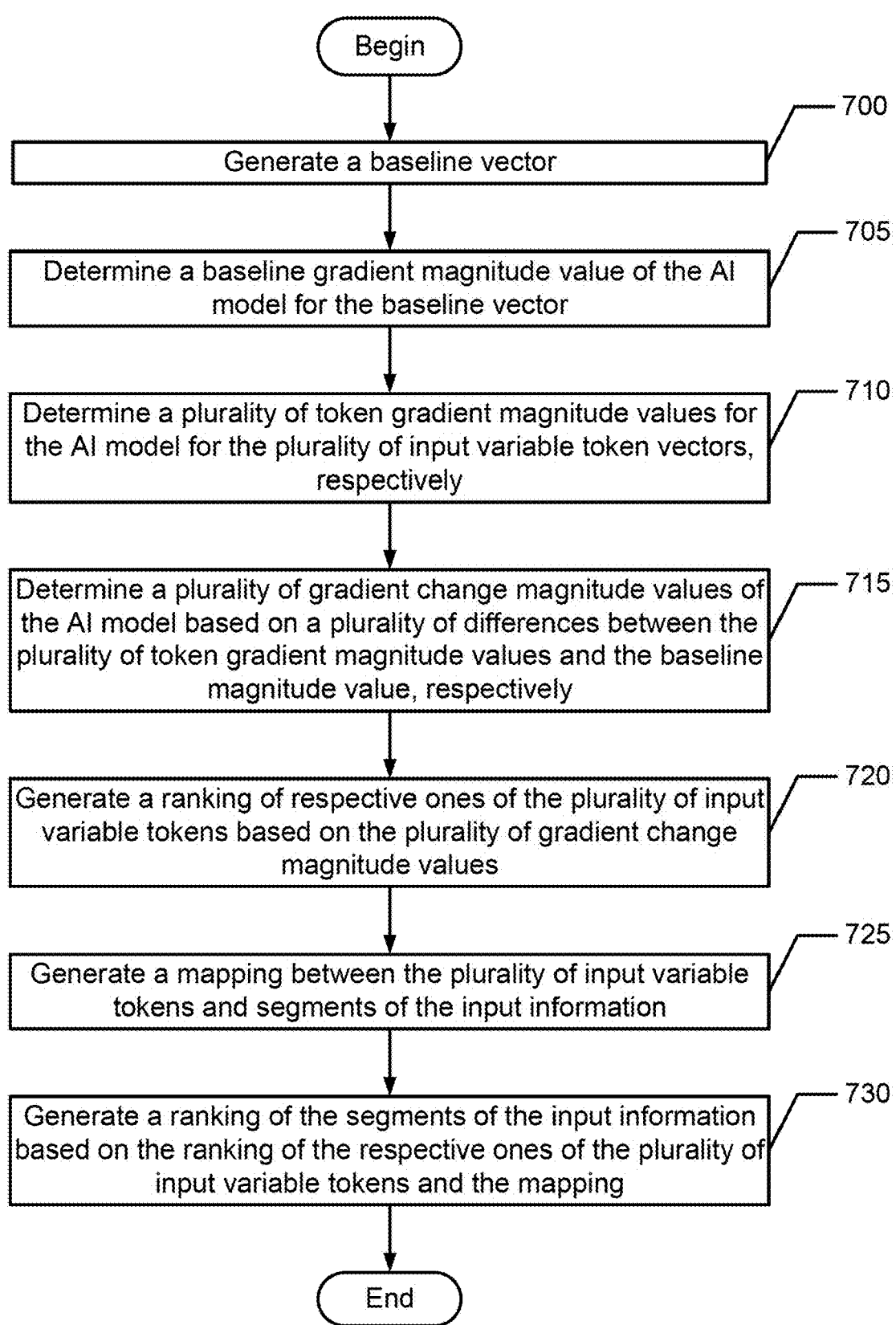

Operations for applying the IG methodology to the multilayer neural network 235 used for selecting criteria subsets for performing a medical necessity review with automatic evidence highlighting will be described hereafter with reference to FIG. 7. Operations begin at block 700 where a baseline vector is defined, which is not representative of any information that affects generating identification of the criterion using the AI model, e.g., multi-layer neural network 235. The baseline vector may be, for example, a vector based on the sentence start and sentence end tokens. A baseline gradient magnitude value of the AI model is determined for the baseline vector at block 705. A plurality of token gradient magnitude values for the AI models for the plurality of input variable token vectors, respectively, is determined at block 710. A plurality of gradient change magnitude values is determined at block 715 based on the plurality of differences between the plurality of token gradient magnitude values and the base line magnitude value, respectively. At block 720, a ranking of the respective ones of the plurality of input variable tokens based on the plurality of gradient change magnitude values is generated. A mapping between the input variable tokens and segments of the input information may be generated at block 725. For example, the input variable tokens may be individual words, codes, acronyms, or groups of such information, whereas the segments of input information may be sentences, paragraphs, medications, lab tests, and/or procedures. A ranking of the segments of input information may be generated at block 730 based on the mapping. This ranking of segments of input information, such as sentences or paragraphs in the patient's health record may provide a case manager with the evidence that supports the recommendation for one or more criteria subsets that can be used to determine the appropriateness of a care plan as part of a medical necessity review.

Figure 8:
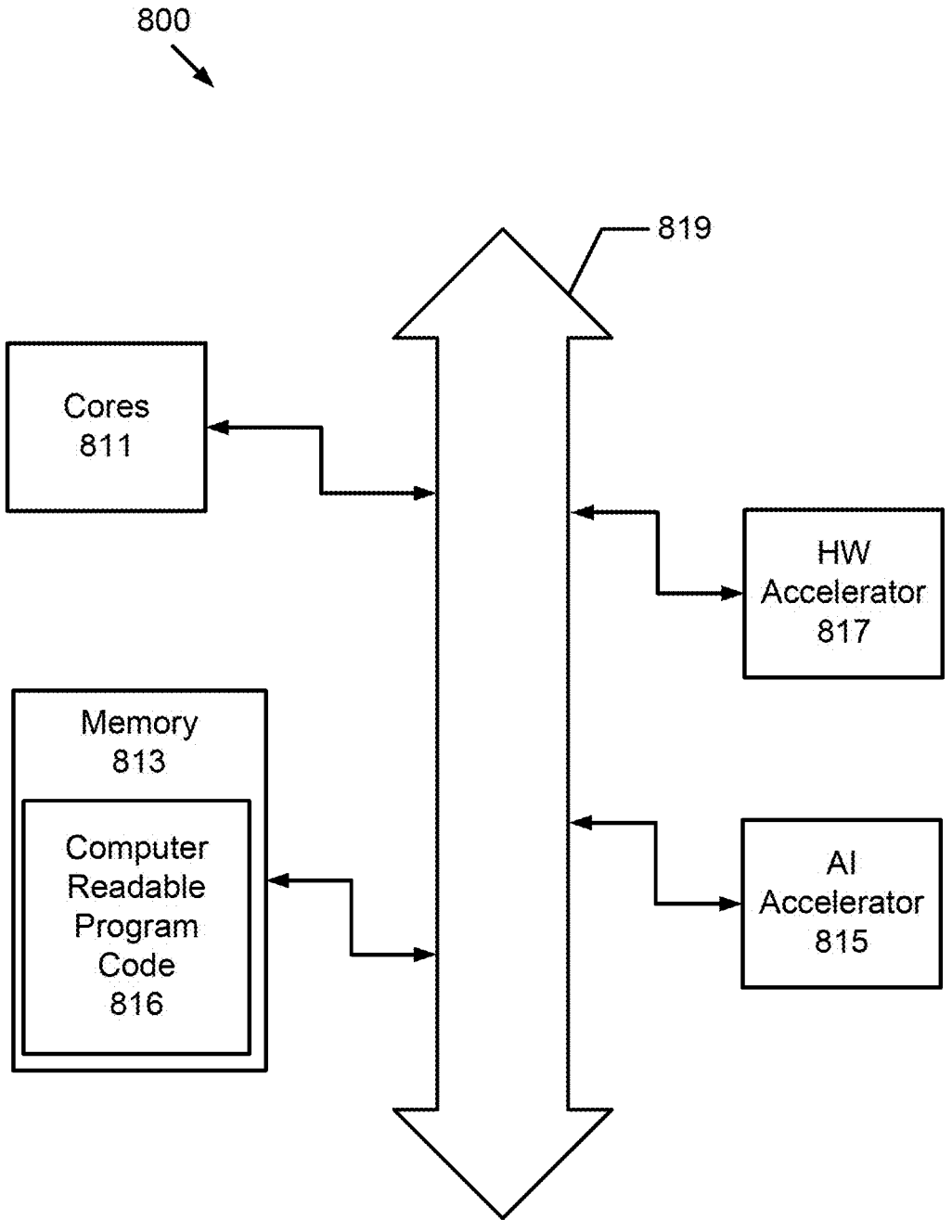
FIG. 8 is a data processing system that may be used to implement a medical necessity review criteria selection system with automatic evidence highlighting in accordance with some embodiments of the inventive concept.

FIG. 8 is a block diagram of a data processing system 800 that may be used to implement the criteria subset selection server 140 of FIG. 1, in accordance with some embodiments of the inventive concept. As shown in FIG. 8, the data processing system 800 may include at least one core 811, a memory 813, an Artificial Intelligence (AI) accelerator 815, and a hardware (HW) accelerator 817. The at least one core 811, the memory 813, the AI accelerator 815, and the HW accelerator 817 may communicate with each other through a bus 819.

The at least one core 811 may be configured to execute computer program instructions. For example, the at least one core 811 may execute an operating system and/or applications represented by the computer readable program code 816 stored in the memory 813. In some embodiments, the at least one core 811 may be configured to instruct the AI accelerator 815 and/or the HW accelerator 817 to perform operations by executing the instructions and obtain results of the operations from the AI accelerator 815 and/or the HW accelerator 817. In some embodiments, the at least one core 811 may be an ASIP customized for specific purposes and support a dedicated instruction set.

The memory 813 may have an arbitrary structure configured to store data. For example, the memory 813 may include a volatile memory device, such as dynamic random-access memory (DRAM) and static RAM (SRAM), or include a non-volatile memory device, such as flash memory and resistive RAM (RRAM). The at least one core 811, the AI accelerator 815, and the HW accelerator 817 may store data in the memory 813 or read data from the memory 813 through the bus 819.

The AI accelerator 815 may refer to hardware designed for AI applications. In some embodiments, the AI accelerator 815 may include medical necessity review system functionality configured to provide a service for selecting one or more subsets of criteria used in determining the appropriateness of a care plan for a patient with automatic evidence highlighting. The AI accelerator 815 may generate output data by processing input data provided from the at least one core 815 and/or the HW accelerator 817 and provide the output data to the at least one core 811 and/or the HW accelerator 817. In some embodiments, the AI accelerator 815 may be programmable and be programmed by the at least one core 811 and/or the HW accelerator 817. The HW accelerator 817 may include hardware designed to perform specific operations at high speed. The HW accelerator 817 may be programmable and be programmed by the at least one core 811.

Figure 9:
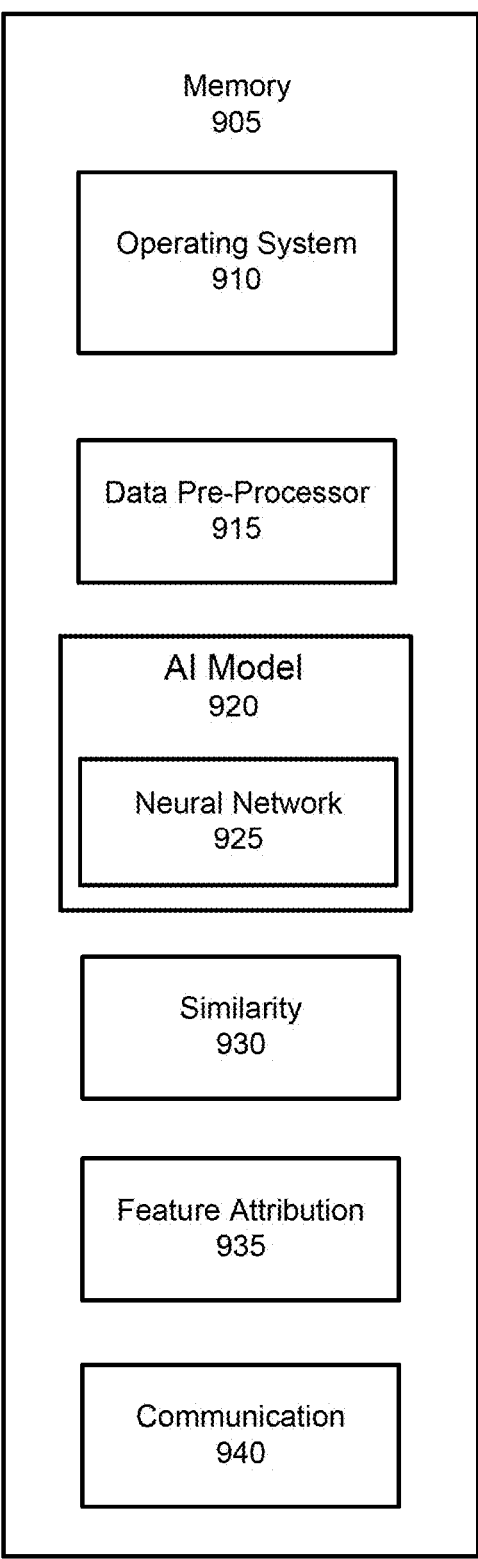
FIG. 9 is a block diagram that illustrates a software/hardware architecture for use in the AI system for selecting criteria subsets with automatic evidence highlighting of FIG. 1 in accordance with some embodiments of the inventive concept.

FIG. 9 illustrates a memory 905 that may be used in embodiments of data processing systems, such as the criteria subset selection server 140 of FIG. 1 and the data processing system 800 of FIG. 8, respectively, to facilitate operation of a system for selecting criteria subsets for use in a medical necessity review with automatic evidence highlighting. The memory 905 is representative of the one or more memory devices containing the software and data used for facilitating operations of the criteria subset selection server 140 as described herein. The memory 905 may include, but is not limited to, the following types of devices: cache, ROM, PROM, EPROM, EEPROM, flash, SRAM, and DRAM. As shown in FIG. 9, the memory 905 may contain six or more categories of software and/or data: an operating system 910, a data pre-processor module 915, an AI model 920, a similarity module 930, a feature attribution module 935, and a communication module 940. In particular, the operating system 910 may manage the data processing system's software and/or hardware resources and may coordinate execution of programs by the processor.

The data pre-processor 915 may be configured to receive and organize the information corresponding to the input variables, e.g., the training feature set 205 and the current input feature set of FIG. 1 when the neural network 235 is in training mode and when the multi-layer neural network 235 is in inference mode, respectively. The AI model module 920 may comprise a neural network module 925. The neural network module 925 may be configured to perform one or more of the operations described above with respect to the neural network 235 and FIGS. 4-7. The similarity module 935 may be configured to implement similarity evaluation functionality, such cosine similarity functionality, including one or more of the operations described above with respect to FIGS. 2-7. The feature attribution module may be configured to perform one or more of the operations described above with respect to the multi-layer neural network 235 and FIG. 7. The communication module 940 may be configured to facilitate communication between the criteria subset selection server 140 of FIG. 1 and entities, such as providers, clinical researchers, and the like.

Although FIGS. 8 and 9 illustrate hardware/software architectures that may be used in data processing systems, such as the criteria subset selection server 140 of FIG. 1 and the data processing system 800 of FIG. 8, respectively, in accordance with some embodiments of the inventive concept, it will be understood that the present invention is not limited to such a configuration but is intended to encompass any configuration capable of carrying out operations described herein.

Computer program code for carrying out operations of data processing systems discussed above with respect to FIGS. 1-9 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the criteria subset selection server 140 of FIG. 1 and the data processing system 800 of FIG. 8 may each be implemented as a single processor system, a multi-processor system, a multi-core processor system, or even a network of standalone computer systems, in accordance with various embodiments of the inventive concept. Each of these processor/computer systems may be referred to as a "processor" or "data processing system." The functionality provided by the health care facility interface server 130 and the criteria subset selection server 140 may be merged into a single server or maintained as separate servers in accordance with different embodiments of the inventive concept.

The data processing apparatus described herein with respect to FIGS. 1-9 may be used to facilitate operation of a medical necessity review criteria selection system with automatic evidence highlighting according to some embodiments of the inventive concept described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 805 when coupled to a processor includes computer readable program code that, when executed by the processor, causes the processor to perform operations including one or more of the operations described herein with respect to FIGS. 1-7.

Some embodiments of the inventive system may provide a medical necessity review criteria selection system that may assist a provider, such as a case manager, in performing a medical necessity review of a care plan for a patient. The medical necessity review criteria selection system makes use of an AI model to identify and/or rank potential subsets, such as InterQual criteria subsets, which are used in performing a medical necessity review for a patient. The medical necessity review criteria selection system further includes automatic evidence highlighting in which an IG methodology is used to categorize those features in the input data to the AI model based on their contribution to the output of the AI model in identifying subsets of criteria. This may provide a case manager, for example, with more confidence in the identification and/or ranking of the one or more criteria subsets and may alleviate the case manager from a burden of reviewing a patient's health record to search manually for evidence supporting one or more criteria subsets used in a medical necessity review.

Further Definitions and Embodiments

In the above description of various embodiments of the present inventive concept, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

The flowchart and block diagrams in the figures illustrate the architecture, functionality, and operation of possible implementations of systems, methods, and computer program products according to various aspects of the present inventive concept. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the inventive concept. As used herein, the singular forms "a", "an" and "the" are intended to include the plural forms as well, unless the context clearly indicates otherwise. It will be further understood that the terms "comprises" and/or "comprising." when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

In the above-description of various embodiments of the present inventive concept, aspects of the present inventive concept may be illustrated and described herein in any of a number of patentable classes or contexts including any new and useful process, machine, manufacture, or composition of matter, or any new and useful improvement thereof. Accordingly, aspects of the present inventive concept may be implemented entirely hardware, entirely software (including firmware, resident software, micro-code, etc.) or combining software and hardware implementation that may all generally be referred to herein as a "circuit," "module," "component," or "system." Furthermore, aspects of the present inventive concept may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

The description of the present inventive concept has been presented for purposes of illustration and description, but is not intended to be exhaustive or limited to the inventive concept in the form disclosed. Many modifications and variations will be apparent to those of ordinary skill in the art without departing from the scope and spirit of the inventive concept. The aspects of the inventive concept herein were chosen and described to best explain the principles of the inventive concept and the practical application, and to enable others of ordinary skill in the art to understand the inventive concept with various modifications as are suited to the particular use contemplated.

What is claimed is:

1. A method comprising:

receiving, by one or more processors, input information associated with a health record of a patient, the input information comprising a plurality of input variable tokens;

embedding, by the one or more processors, the plurality of input variable tokens using a natural language processing embedding module to generate a plurality of input variable token vectors, respectively;

aggregating, by the one or more processors, the plurality of input variable token vectors to generate a patient health record vector;

generating an identification of a criterion used for determining an appropriateness of a care plan for the patient based on the patient health record vector, by the one or more processors using an application specific integrated circuit (ASIC) for an artificial neural network including an input layer having a first plurality of neurons corresponding to the plurality of input variable token vectors, a plurality of hidden layers having a second plurality of neurons, and an output layer having a third plurality of neurons each corresponding to a different criteria subset for determining the appropriateness of the care plan for the patient, wherein the first and second pluralities of neurons have associated weights that pass data from one layer to another layer in response to determining that an output of a rectified linear unit (ReLU) activation function exceeds a threshold after performing a multiply-accumulate (MAC) operation on inputs to one of the first and second pluralities of neurons using the associated weights;

generating, by the one or more processors using the artificial neural network, a ranking of respective ones of the plurality of input variable tokens based on how much each of the plurality of input variable tokens contributed to the identification of the criterion used for determining the appropriateness of the care plan; and providing, by the one or more processors, automatic evidence highlighting of the patient health record using the ranking of the respective ones of the plurality of input variable tokens to identify specific clinical information within the patient health record which contributed most to identifying the criterion used for determining the appropriateness of the care plan.

2. The method of claim 1, wherein generating the ranking of the respective ones of the plurality of input variable tokens comprises:

generating, by the one or more processors, the ranking of the respective ones of the plurality of input variable tokens using an Integrated Gradient (IG) methodology.

3. The method of claim 2, wherein generating the ranking of the respective ones of the plurality of input variable tokens using the IG methodology comprises:

generating, by the one or more processors, a baseline vector;

determining, by the one or more processors, a baseline gradient magnitude value of the artificial neural network for the baseline vector;

determining, by the one or more processors, a plurality of token gradient magnitude values of the artificial neural network for the plurality of input variable token vectors, respectively;

determining, by the one or more processors, a plurality of gradient change magnitude values of the artificial neural network based on a plurality of differences between the plurality of token gradient magnitude values and the baseline gradient magnitude value, respectively; and generating, by the one or more processors, the ranking of the respective ones of the plurality of input variable tokens based on the plurality of gradient change magnitude values.

4. The method of claim 3, wherein the baseline vector is not representative of any information that affects generating identification of the criterion using the artificial neural network.

5. The method of claim 3, further comprising:

generating, by the one or more processors, the plurality of input variable tokens using a bidirectional transformer;

wherein embedding the plurality of input variable tokens to generate the plurality of input variable token vectors comprises:

embedding, by the one or more processors, the plurality of input variable tokens to generate the plurality of input variable token vectors using the bidirectional transformer.

6. The method of claim 5, wherein the bidirectional transformer is a Clinical Bidirectional Encoder Representations from Transformers (ClinicalBERT) bidirectional transformer.

7. The method of claim 3, further comprising:

generating, by the one or more processors, a mapping between the plurality of input variable tokens and segments of the input information.

8. The method of claim 7, further comprising:

generating, by the one or more processors, a ranking of the segments of the input information based on the ranking of the respective ones of the plurality of input variable tokens and the mapping.

9. The method of claim 8, wherein the segments of the input information comprise sentences, medications, lab tests, and/or procedures.

10. A system, comprising:

an application-specific integrated circuit (ASIC);

one or more processors; and one or more memories storing processor-executable instructions that, when executed by the one or more processors, cause the one or more processors to perform operations comprising:

receiving input information associated with a health record of a patient, the input information comprising a plurality of input variable tokens;

embedding the plurality of input variable tokens using a natural language processing embedding module to generate a plurality of input variable token vectors, respectively;

aggregating the plurality of input variable token vectors to generate a patient health record vector;

generating an identification of a criterion used for determining an appropriateness of a care plan for the patient based on the patient health record vector, using the ASIC for an artificial neural network including an input layer having a first plurality of neurons corresponding to the plurality of input variable token vectors, a plurality of hidden layers having a second plurality of neurons, and an output layer having a third plurality of neurons each corresponding to a different criteria subset for determining an appropriateness of a care plan for the patient, wherein the first and second pluralities of neurons have associated weights that pass data from one layer to another layer in response to determining that an output of a rectified linear unit (ReLU) activation function exceeds a threshold after performing a multiply-accumulate (MAC) operation on inputs to one of the first and second pluralities of neurons using the associated weights;

generating, using the artificial neural network, a ranking of respective ones of the plurality of input variable tokens based on how much each of the plurality of input variable tokens contributed to the identification of the criterion used for determining the appropriateness of the care plan; and providing automatic evidence highlighting of the patient health record using the ranking of the respective ones of the plurality of input variable tokens to identify specific clinical information within the patient health record which contributed most to identifying the criterion used for determining the appropriateness of the care plan.

11. The system of claim 10, wherein generating the ranking of the respective ones of the plurality of input variable tokens comprises:

generating the ranking of the respective ones of the plurality of input variable tokens using an Integrated Gradient (IG) methodology.

12. The system of claim 11, wherein generating the ranking of the respective ones of the plurality of input variable tokens using the IG methodology comprises:

generating a baseline vector;

determining a baseline gradient magnitude value of the artificial neural network for the baseline vector;

determining a plurality of token gradient magnitude values of the artificial neural network for the plurality of input variable token vectors, respectively;

determining a plurality of gradient change magnitude values of the artificial neural network based on a plurality of differences between the plurality of token gradient magnitude values and the baseline gradient magnitude value, respectively; and generating the ranking of the respective ones of the plurality of input variable tokens based on the plurality of gradient change magnitude values.

13. The system of claim 12, wherein the operations further comprise:

generating the plurality of input variable tokens using a bidirectional transformer;

wherein embedding the plurality of input variable tokens to generate the plurality of input variable token vectors comprises:

embedding the plurality of input variable tokens to generate the plurality of input variable token vectors using the bidirectional transformer.

14. The system of claim 12, wherein the operations further comprise:

generating a mapping between the plurality of input variable tokens and segments of the input information.

15. The system of claim 14, wherein the operations further comprise:

generating a ranking of the segments of the input information based on the ranking of the respective ones of the plurality of input variable tokens and the mapping.

16. One or more non-transitory computer-readable media storing processor-executable instructions that, when executed by one or more processors, cause the one or more processors to perform operations comprising:

receiving input information associated with a health record of a patient, the input information comprising a plurality of input variable tokens;

embedding the plurality of input variable tokens using a natural language processing embedding module to generate a plurality of input variable token vectors, respectively;

aggregating the plurality of input variable token vectors to generate a patient health record vector;

generating an identification of a criterion used for determining a appropriateness of a care plan for the patient based on the patient health record vector, using an artificial neural network in an application-specific integrated circuit (ASIC) including an input layer having a first plurality of neurons corresponding to the plurality of input variable token vectors, a plurality of hidden layers having a second plurality of neurons, and an output layer having a third plurality of neurons each corresponding to a different criteria subset for determining the appropriateness of the care plan for the patient, wherein the first and second pluralities of neurons have associated weights that pass data from one layer to another layer in response to determining that an output of a rectified linear unit (ReLU) activation function exceeds a threshold after performing a multiply-accumulate (MAC) operation on inputs to one of the first and second pluralities of neurons using the associated weights;

generating, using the artificial neural network, a ranking of respective ones of the plurality of input variable tokens based on how much each of the plurality of input variable tokens contributed to the identification of the criterion used for determining the appropriateness of the care plan; and providing automatic evidence highlighting of the patient health record using the ranking of the respective ones of the plurality of input variable tokens to identify specific clinical information within the patient health record which contributed most to identifying the criterion used for determining the appropriateness of the care plan.

17. The one or more non-transitory computer-readable claim 16, wherein generating the ranking of the respective ones of the plurality of input variable tokens comprises:

generating a baseline vector;

determining a baseline gradient magnitude value of the artificial neural network for the baseline vector;

determining a plurality of token gradient magnitude values of the artificial neural network for the plurality of input variable token vectors, respectively;

determining a plurality of gradient change magnitude values of the artificial neural network based on a plurality of differences between the plurality of token gradient magnitude values and the baseline gradient magnitude value, respectively; and generating the ranking of the respective ones of the plurality of input variable tokens based on the plurality of gradient change magnitude values.

18. The one or more non-transitory computer-readable claim 17, wherein the operations further comprise:

generating the plurality of input variable tokens using a bidirectional transformer;

wherein embedding the plurality of input variable tokens to generate the plurality of input variable token vectors comprises:

embedding the plurality of input variable tokens to generate the plurality of input variable token vectors using the bidirectional transformer.

19. The one or more non-transitory computer-readable claim 16, wherein the operations further comprise:

generating a mapping between the plurality of input variable tokens and segments of the input information.

20. The one or more non-transitory computer-readable claim 19, wherein the operations further comprise:

generating a ranking of the segments of the input information based on the ranking of the respective ones of the plurality of input variable tokens and the mapping.

* * * * *